(12) United States Patent
Evans

(10) Patent No.: US 10,137,026 B2
(45) Date of Patent: Nov. 27, 2018

(54) WATER RESISTANT BANDAGE

(71) Applicant: BSN, Medical, Inc., Charlotte, NC (US)

(72) Inventor: John C. Evans, Nr Rochdale (GB)

(73) Assignee: BSN MEDICAL, INC., Charlotte, NC (US)

( * ) Notice: Subject to any disclaimer, the term of this patent is extended or adjusted under 35 U.S.C. 154(b) by 412 days.

(21) Appl. No.: 14/616,140

(22) Filed: Feb. 6, 2015

(65) Prior Publication Data
US 2015/0150710 A1    Jun. 4, 2015

Related U.S. Application Data

(63) Continuation of application No. 12/438,553, filed as application No. PCT/US2009/034838 on Feb. 23, 2009.

(60) Provisional application No. 61/147,222, filed on Jan. 26, 2009.

(51) Int. Cl.
| | |
|---|---|
| A61F 15/00 | (2006.01) |
| A61F 5/05 | (2006.01) |
| A61F 13/00 | (2006.01) |
| A61F 13/06 | (2006.01) |
| D04B 21/18 | (2006.01) |
| A61F 13/08 | (2006.01) |
| A61F 13/10 | (2006.01) |
| A61F 13/02 | (2006.01) |

(52) U.S. Cl.
CPC .......... *A61F 5/05* (2013.01); *A61F 13/00017* (2013.01); *A61F 13/00038* (2013.01); *A61F 13/00046* (2013.01); *A61F 13/069* (2013.01); *A61F 13/085* (2013.01); *A61F 13/108* (2013.01); *D04B 21/18* (2013.01); *A61F 13/0273* (2013.01); *A61F 2013/00119* (2013.01); *A61F 2013/00238* (2013.01); *A61F 2013/00246* (2013.01); *A61F 2013/00263* (2013.01); *A61F 2013/00876* (2013.01); *D10B 2403/0114* (2013.01); *D10B 2509/028* (2013.01)

(58) Field of Classification Search
CPC .................. A61F 13/02; A61F 13/0243; A61F 13/00017; A61F 13/00021; A61F 13/00029; A61F 13/00; A61F 13/00046; A61F 2013/00604
USPC .............................. 602/3, 43, 44, 53, 75, 76
See application file for complete search history.

(56) References Cited

U.S. PATENT DOCUMENTS

| | | | | |
|---|---|---|---|---|
| 4,366,814 A | * | 1/1983 | Riedel | A61L 15/24 |
| | | | | 428/197 |
| 4,665,909 A | * | 5/1987 | Trainor | A61F 13/0273 |
| | | | | 602/75 |

(Continued)

OTHER PUBLICATIONS

Spencer; "Knitting Technology"; 2nd edition—p. 36.*

*Primary Examiner* — Ophelia A Hawthorne
*Assistant Examiner* — Caitlin Carreiro
(74) *Attorney, Agent, or Firm* — Shumaker, Loop & Kendrick, LLP (57) ABSTRACT

A water resistant light compression and/or retention bandage for retaining an orthopedic splint, padding or medical device against a body part, includes a knitted fabric formed of synthetic yarns having a moisture vapor transmission rate from an inner face of the bandage to an outer face of the bandage of at least 500 g/m² per 24 hours.

14 Claims, 5 Drawing Sheets

(56) References Cited

U.S. PATENT DOCUMENTS

| | | | | |
|---|---|---|---|---|
| 4,745,912 A | * | 5/1988 | McMurray | A61F 13/04 602/8 |
| 5,086,150 A | * | 2/1992 | Frauendorf | C08G 18/0852 521/137 |
| 2005/0186871 A1 | * | 8/2005 | Hockaday | A61L 2/232 442/76 |
| 2008/0287852 A1 | * | 11/2008 | Evans | A61F 13/041 602/43 |

* cited by examiner

WATER RESISTANT BANDAGE

TECHNICAL FIELD AND BACKGROUND OF THE INVENTION

The present invention provides an elasticized water resistant bandage that may have light compression and/or retention characteristics for use in orthopaedic applications. More specifically, the bandage is used to hold a splint, wound dressing, padding or medical device in position against the limb or anatomy of the patient. The knitted retention bandage is water resistant so in combination with the splint, padding, or medical device that is regarded as water resistant, it can maintain the injury site in a dry and comfortable condition. The bandage may also provide a degree of compression to the surrounded body part, often a limb, that may improve circulation at and near the injury site.

The knitted elasticized retention bandage of the present invention is highly breathable with a moisture vapor transmission rate of greater than 1400 g/m² per 24 hours. The present knitted construction of the elasticized light compression water resistant retention bandage involves a novel use of single monofilament yarns and knitting notation to render the bandage non-slip and therefore able to secure a splint, padding or medical device in position against movement in order to enable the splint, padding or other medical device to properly accomplish their desired medical effects.

Conventional bandages that are used to keep injury sites dry and clean rely on yarns and fibers that wick moisture away from the skin to the surface of the bandage. This construction is intended to enable the natural heat from the body and circulating air to dissipate the excess moisture. However, in practice, these conventional bandages can be overwhelmed by the amount of moisture wicked into their structure, particularly in ambient conditions of high humidity and/or low temperature where moisture transfer rates are compromised. Increasing the density of the structure to allow it to absorb more moisture further reduces the ability of the moisture to be transferred as vapor into the surrounding air. In general, the prior art has moved in a counterproductive direction in attempts to solve this problem.

In contrast, the bandage according to the embodiments described and claimed is formed from non-absorbent materials in a very lightweight, open fabric construction that allows excess water to drain from the bandage and be exposed to circulating air in and around the bandage to dry off the skin and allow moisture transfer into the surrounding air from the bandage. This has been found to be a much more effective way of keeping the injury and surrounding areas dry and allows the patient to bathe or shower without fear of getting the injury site wetted to the point that the moisture cannot be effectively dissipated.

This novel water resistant bandage has been tested to Standard BS7505 relating to "Elastic Properties of Extensible Bandages."

SUMMARY OF THE INVENTION

Accordingly, it is an object of the invention to provide a retention bandage suitable for use over orthopaedic bandages such as splints.

It is another object of the invention to provide a light compression bandage suitable for use over orthopaedic bandages such as splints.

It is another object of the invention to provide a bandage that has both light compression and retention characteristics suitable for use over orthopaedic bandages such as splints.

It is another object of the invention to provide a bandage that efficiently moves moisture away from the skin and orthopaedic bandage.

It is another object of the invention to provide a bandage suitable for use over orthopaedic bandages such as splints that has an open construction that is lightweight and breathable.

It is another object of the invention to provide a bandage suitable for use over orthopaedic bandages such as splints that is lightweight, breathable with sufficient elasticity to comprise a light compression bandage.

These and other objects and advantages of the invention are achieved by providing an elongate bandage for overwrapping and retaining an underlying medical device in position on a body part, and comprising a knitted fabric formed of synthetic yarns having a moisture vapor transmission rate from an inner face of the bandage to an outer face of the bandage of at least 500 g/m² per 24 hours.

According to one preferred embodiment of the invention, the fabric includes elastic yarns and has an elongation in a lengthwise direction of at least 30% of its relaxed length.

According to another preferred embodiment of the invention, the inner face of the knitted fabric comprises a soft yarn for application against the medical device and the skin of a patient; and the outer face of the knitted fabric comprises a hydrophobic yarn for transmitting moisture away from the inner face of the bandage.

According to another preferred embodiment of the invention, the soft yarn of the inner face and the hydrophobic yarns of the outer face are both monofilament yarns.

According to another preferred embodiment of the invention, the fabric includes windows in the fabric that in a relaxed state is between 380 and 640/m², the number of courses in the weft direction in a relaxed state is between 5 and 12 per cm²; and the weight of the fabric in a relaxed state is 70+/−5 gsm².

According to another preferred embodiment of the invention, the yarns of the inner face are Nylon 1/33 dtex and the yarns of the outer face are 0.1 polypropylene.

According to another preferred embodiment of the invention, the bandage includes elastic threads of either, polyester, polyurethane, nylon or polyether that can be covered or uncovered in the preferred embodiment the elastic threads are an uncovered polyurethane.

According to another preferred embodiment of the invention, an elongate bandage is provided for overwrapping and retaining an underlying medical device in position on a body part, and comprises a knitted fabric formed of synthetic yarns having a moisture vapor transmission rate from an inner face of the bandage to an outer face of the bandage of at least 500 g/m² per 24 hours. The inner face of the knitted fabric comprises a soft monofilament synthetic yarn for application against the medical device and the skin of a patient; the outer face of the knitted fabric comprises a monofilament hydrophobic yarn for transmitting moisture away from the inner face of the bandage, and the number of windows in the fabric in a relaxed state is between 380 and 640/m², the number of courses in the weft direction in a relaxed state is between 5 and 12 per cm²; and the weight of the fabric in a relaxed state is 70+/−5 gsm².

According to another preferred embodiment of the invention, the bandage includes elastic yarns and has an elongation in a lengthwise direction of at least 30%.

According to another preferred embodiment of the invention, an elongate bandage is provided for overwrapping and retaining an underlying medical device in position on a body part, and comprises a warp-knitted fabric having a moisture vapor transmission rate from an inner face of the bandage to an outer face of the bandage of at least 500 g/m² per 24 hours. The fabric includes nylon yarns formed into loops on the inner face that protrude through the thickness of the fabric to the outer face to promote moisture transmission through the thickness of the fabric.

According to another preferred embodiment of the invention, the moisture vapor transmission rate is at least 1400 g/m² per 24 hours.

According to another preferred embodiment of the invention, the bandage includes a plurality of fine elastic threads, knitted or laid in with the wales to improve the stretch characteristics of the fabric structure to improve conformability to the anatomy of the patient.

According to another preferred embodiment of the invention, the elastic threads are knitted or laid into a chain stitch formed in the fabric, the elastic threads having a modulus of elasticity ≤90 Cn at breaking elongation ≥470%.

According to another preferred embodiment of the invention, a water resistant light compression retention bandage is provided for retaining an orthopaedic splint, padding or medical device against a body part. The bandage comprises a fabric structure defining an inner face of relatively soft synthetic yarns suitable for contact with body part, and an outer face that comprises a plurality of wales constructed of hydrophobic monofilament yarns and a plurality of courses that are inserted in the knitted yarn that create windows that allow for breathability and conformability of the fabric to the body part and overlying splint, padding or medical device. A plurality of fine elastic threads are knitted or laid in with the wales to improve the stretch characteristics of the fabric structure and to aid and improve conformability to the anatomy of the patient.

BRIEF DESCRIPTION OF THE DRAWINGS

Some of the objects of the invention have been set forth above. Other objects and advantages of the invention will appear as the description of the invention proceeds when taken in conjunction with the following drawings, in which.

DESCRIPTION OF THE PREFERRED EMBODIMENTS AND BEST MODE

Figure 1:
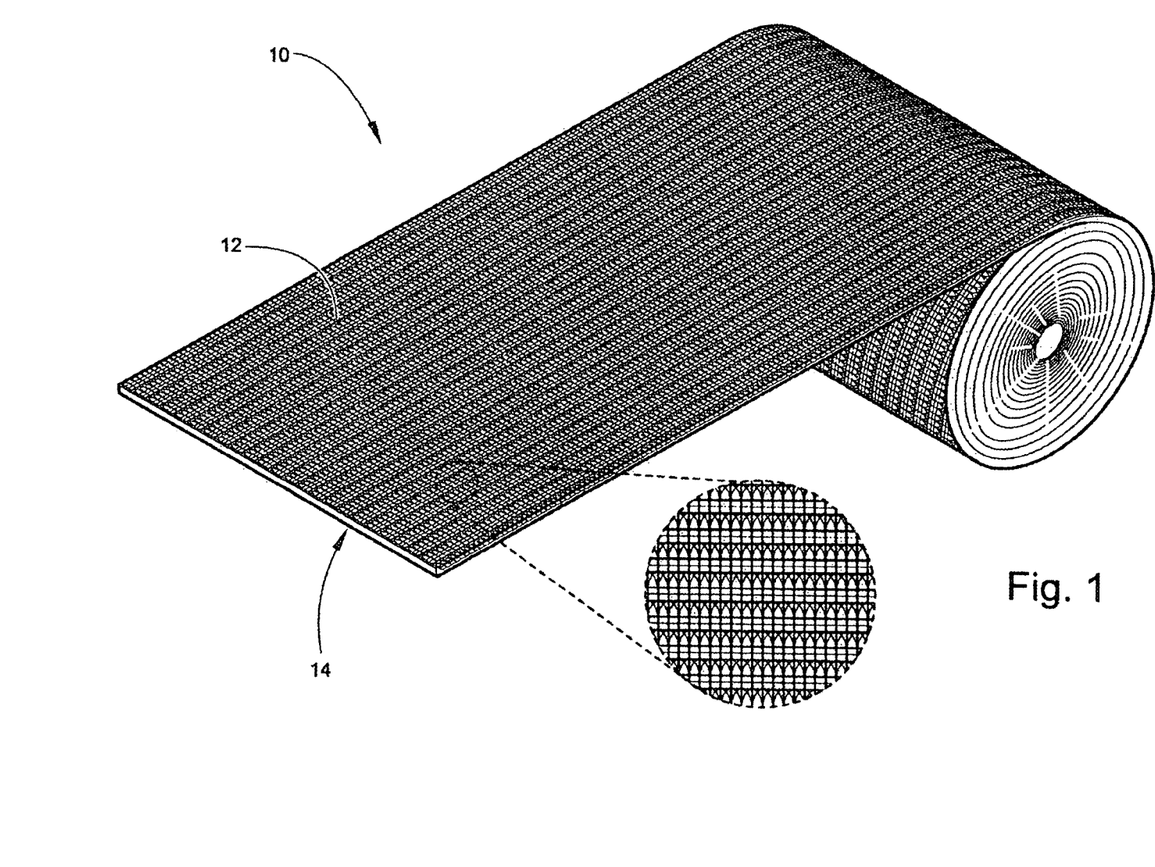
FIG. 1 is a view of one embodiment of the novel light compression and retention bandage.

Referring now specifically to the drawings, a retention bandage according to a preferred embodiment of the present invention is shown generally in FIG. 1 at reference numeral 10.

The knitted structure of the bandage 10 preferably includes a combination of nylon and polypropylene monofilament yarns and, in addition, a small amount of elastic. The knit construction gives the fabric a thickness that is greater than the thickness of the yarns themselves and is thus considered three dimensional. This three dimensional characteristic is shown along the facing edge and cut end of the bandage 10 in FIG. 1, and provides separation between the bandage's major opposing outer and inner faces 12 and 14. The bandage 10 is typically rolled as shown in FIG. 1 for ease in packaging and in manipulating the bandage 10 onto the injured limb.

The nylon is the softer of the two fibers and is knitted into the structure in a manner whereby the nylon is on the inner face 14 and therefore against the body part, with the polypropylene outer face 12 facing outwardly and not contacting the skin. The polypropylene is the more resilient of the fibers and has natural hydrophobic properties. The polypropylene therefore provides enhanced stability to the construction and acts as the drainage medium for moisture.

Elastic yarns are preferably incorporated into the fabric structure of the bandage 10 to provide additional elasticity. One suitable elastic yarn is Dorlastan, a filament fiber of segmented polyester- or polyether/polyurethane. A relatively small amount of this fiber is sufficient to obtain elasticity, elastic recovery and dimensional stability.

The knitted construction of the bandage 10 uses monofilament yarns that are very fine, generally having a maximum diameter of 0.1 mm. This allows for a very open knitted structure and extremely low weight which promotes rapid moisture transmission through the thickness of the fabric from the nylon inner face 14 to the polypropylene outer face 12, and into ambient air.

One exemplary embodiment of the bandage 10 is set out below:

Example 1

18 Gauge Single Bar Warp Knitting Machine Equipped with 4 Bars

Threading and Run-In

Bar 1 and 2 fully threaded, PP 0.1 Plasticel Polypropylene,

Run-Ins 1650 mm/Rack,

Bar 3 Fully Threaded, Nylon 1/33 dtex, Run-Ins 2550 mm/rack.

Bar 4 Half Threaded with ends in first and last needle,

Elastic Dorlastan 1/80 dtex, Run-Ins 550 mm/rack. Beaming Tension 50%.

Bandage Details 73 needles for 3" bandage.

97 needles for 4" bandage.

49 needles for 2" bandage.

Fabric Specifications 700 courses per meter "cpm" on machine.

900-950 cpm out of roll.

70+/−5 gsm² relaxed fabric weight.

| | |
|---|---|
| Thickness in relaxed state. | 1.26 mm |
| Thickness in stretched (140% of relaxed) state. | 0.85 mm |

Notation of Structure 1-0/0-1 Full Sett Polypropylene Mono.
0-0/4-4 Full Sett Nylon.
1-1/0-0 Half Sett Elastic.

The above-referenced bandage has been tested to Standard BS7505, "Elastic Properties of Extensible Bandages". The test is conducted on a Instron Tensile testing machine and is used to characterize a bandage by measuring its elastic properties using information obtained from the second retraction curve. The test indicates that the bandage 10 of Example 1 meets a Type 2 characterization for application of light compression.

Figure 2:
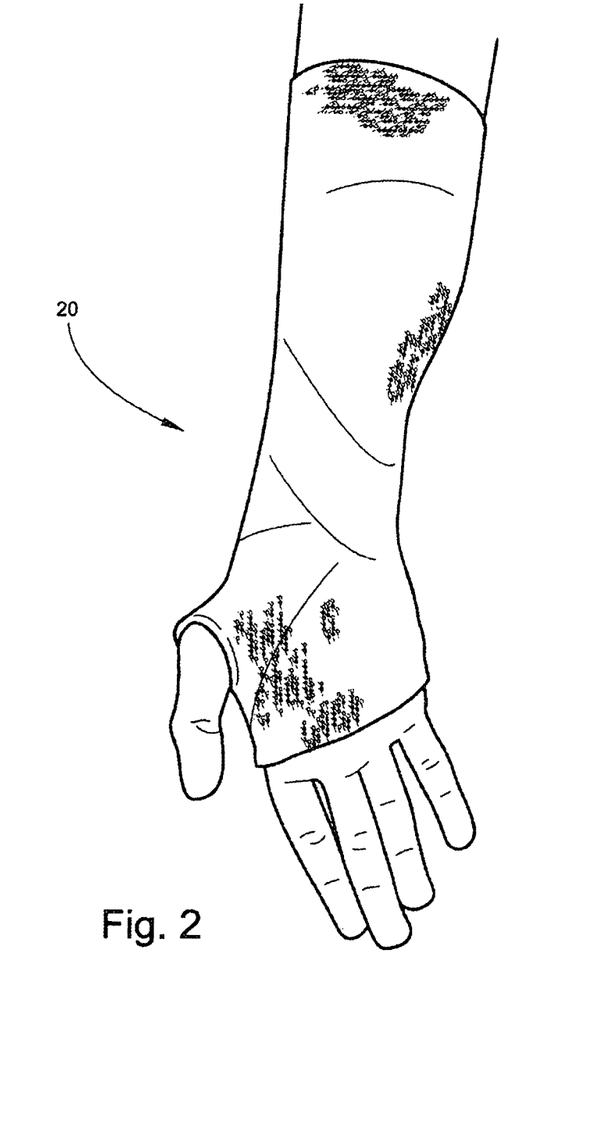
FIG. 2 is a view of a cast bandage of a type over which an embodiment of the light compression and retention bandage shown in FIG. 1 would be wrapped.

FIG. 2 shows a forearm splint 20 of the general type over which the bandage 10 is placed. The splint 20 may be of any type or construction, including plaster/gauze or synthetic cast tape.

Figure 3:
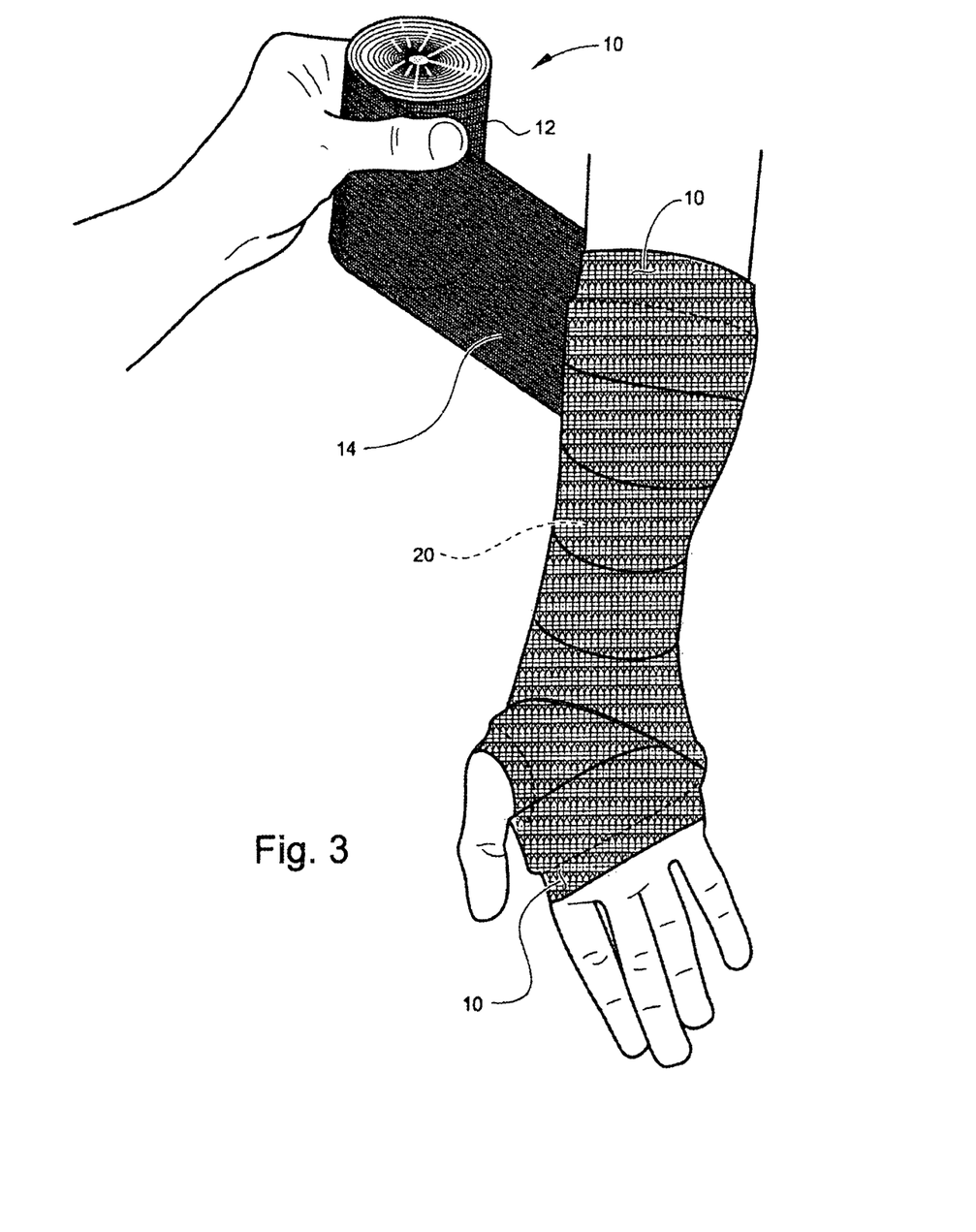
FIG. 3 shows application of the light compression and retention bandage.
Figure 4:
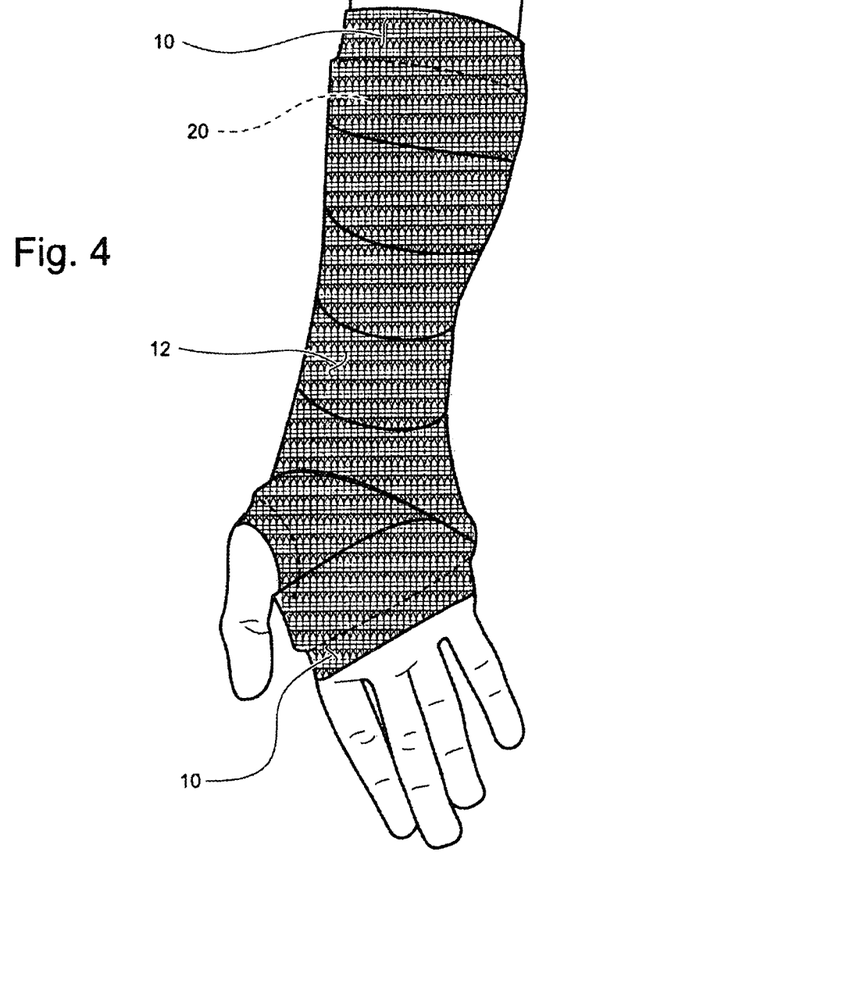
FIG. 4 shows the splint with the light compression and retention bandage in place over the splint.

As is shown in FIG. 3, the bandage 10 is wrapped around the limb and overlying splint 20 with sufficient tension to maintain the splint 20 in its required location and shape. As is shown in FIG. 4, when application is completed the bandage 10 overlaps the splint 20 and contacts the skin on opposite ends of the splint 20. The bandage 10 is applied with nylon inner face 14 against the skin in the manner shown. The nylon yarns create a "channel" effect that allows moisture underneath the bandage 10 to migrate through the bandage 10 to the polypropylene yarns of the outer face 12. To facilitate the movement of moisture, nylon loops of the inner face 14 protrude through the thickness of the fabric to the polypropylene outer face 12.

Suitable embodiments of the bandage include a fabric structure defining an inner face, and an outer face that comprise a plurality of wales (warp yarns) that are constructed of hydrophobic single monofilament threads, and a plurality of courses (weft yarns) that are inserted in the wales yarn that creates holes or windows that allow for breathability and conformability of the structure. The bandage may also include a plurality of fine elastic threads, knitted or laid in with the wales to improve the stretch characteristics of the fabric structure to improve conformability to the anatomy of the patient.

The moisture vapor transmission rate of the fabric of one embodiment of the bandage 10 is not less than 500 g/m$^2$ per 24 hours. The moisture vapor transmission rate of the fabric of other embodiments of the bandage 10 may be as much as not less than 1400 g/m$^2$ per 24 hours. The bandage 10 may be provided with a release and lock closure system, such as hook and loop fasteners, to secure the bandage to the patient. Patches of conventional hook material are secured at or near both ends of the bandage 10 to assist in self-application. Other fasteners, such as adhesive tapes with release liners and landing areas may be used.

The knitted stretchable fabric of the bandage 10 may also include polypropylene monofilament yarns knitted into the chain stitch, and nylon monofilament yarns in both the chain stitch and inlay stitch, with the elastic yarn laid or knitted in the warp or chain stitch direction.

The number of holes or windows in the knitted structure of the bandage 10 in a relaxed state is between 380 and 640/m$^2$, and the number of threads or courses in the weft direction is between 5 and 12 per cm$^2$ in a relaxed state. A typical length of the bandage 10 is between 4.4 m and 5.1 m.

The weight per unit area of the bandage 10 is preferably between 30 and 90 grams per m$^2$ and the stretch of the bandage 10 in the lengthways direction is between 30% AND 75%. The widthways stretch of the bandage 10 in a relaxed state is preferably between 25% and 45%.

The monofilament yarns may be between 0.03 and 0.14 mm in diameter, with a tenacity between 45 and 60 centinewtons/Tex, and the elastic fiber may be between 40 and 80 d/tex. The thickness range of preferred embodiments of a bandage according to the application is 1.1 mm to 2.6 mm in its relaxed state and 0.6 mm to 1.5 mm in a 40% stretched state.

Preferably, the elastic thread is knitted or laid into the chain stitch and has a modulus of elasticity ≤90 Cn at breaking elongation ≥470%. Alternatively, the elastic threads may be synthetic rubber or natural rubber.

Figure 5:
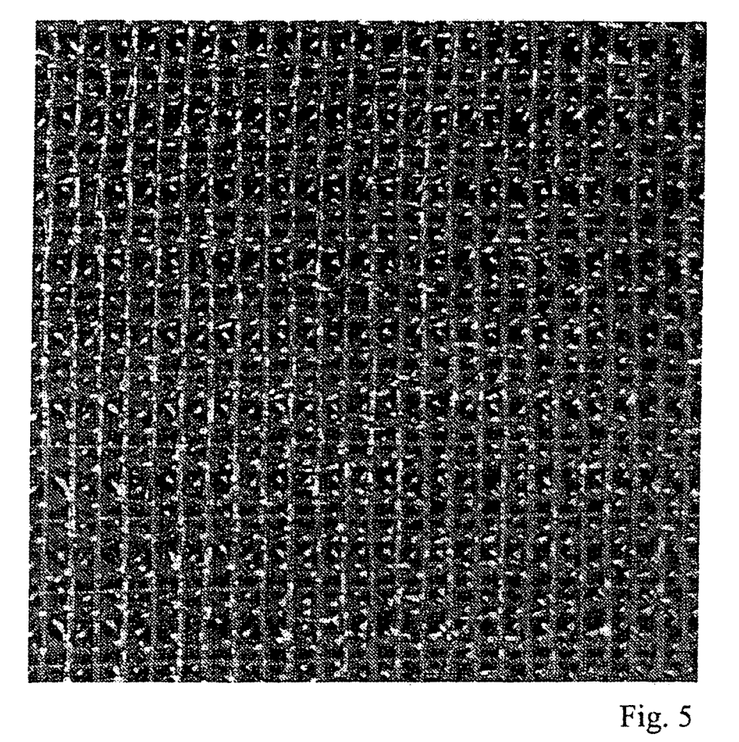
FIG. 5 is a photograph, enlarged in scale, of an embodiment of a light compression and retention bandage according to the preferred embodiment of the invention disclosed in this application.

A photograph of fabric of the bandage 10, enlarged to show detail, is shown in FIG. 5.

An improved medical bandage is described above. Various details of the invention may be changed without departing from the scope of the invention. Furthermore, the foregoing description of the preferred embodiment of the invention and best mode for practicing the invention are provided for the purpose of illustration only and not for the purpose of limitation, the invention being defined by the claims.

What is claimed is:

1. A knitted bandage, consisting of:
an inner face adapted to be positioned contacting skin and an outer face adapted to be positioned apart from the skin;
nylon monofilament yarns knitted into only the inner face and having a maximum diameter of 0.1 mm;
polyproylene monofilament yarns knitted into only the outer face and having a maximum diameter of 0.1 mm; and
elastic yarns knitted or laid in with wales of the knitted bandage to impart elasticity in the knitted bandage;
wherein the knitted bandage has a moisture vapor transmission rate of at least 500 g/m$^2$ per 24 hours.

2. The knitted bandage of claim 1, wherein the polypropylene monofilament yarns are knitted into a chain stitch of the knitted bandage, the nylon monofilament yarns are knitted into both the chain stitch and an inlay stitch of the knitted fabric, and the elastic yarns are laid or knitted in a warp or chain stitch direction.

3. The knitted bandage of claim 1, wherein the outer face of the knitted bandage has a greater hydrophobicity than the inner face of the knitted bandage.

4. The knitted bandage of claim 3, wherein the nylon monofilament yarns of the inner face are formed into loops that protrude through a knitted fabric thickness of the polypropylene monofilament yarn of the outer face.

5. The knitted bandage of claim 1, wherein the elastic yarns comprise a segmented polyester or polyether/polyurethane.

6. The knitted bandage of claim 5, wherein the elastic yarns have a modulus of elasticity ≤90 Cn at a breaking elongation of ≥470%.

7. The knitted bandage of claim 1, wherein the knitted bandage has windows ranging between 380 and 640/m$^2$.

8. The knitted bandage of claim 1, wherein the knitted bandage includes a number of courses in a weft direction in a relaxed state that is between 5 and 12 per cm$^2$, and a weight of the knitted bandage in a relaxed state is 70+/−5 gsm$^2$.

9. The knitted bandage of claim 1, wherein the inner and outer faces are formed of single monofilament yarns having a maximum diameter of 0.1 mm.

10. The knitted bandage of claim 1, wherein yarns of the inner face are nylon 1/33 dtex monofilament yarn, and yarns of the outer face are 0.1 mm polypropylene monofilament yarn.

11. The knitted bandage of claim 1, wherein the knitted bandage has a lengthwise directional stretch of at least 30% and up to 75% in a relaxed state.

12. The knitted bandage of claim 1, wherein the knitted bandage has a widthwise directional stretch of between 25% and 45% in a relaxed state.

13. The knitted bandage of claim 1, wherein the knitted bandage has a thickness ranging from 1.1 mm to 2.6 mm in a relaxed state and from 0.6 mm to 1.5 mm in a stretched state.

14. The knitted bandage of claim 1, wherein a hook fastener is positioned on one end of the knitted bandage and a complimentary loop fastener is positioned on an opposing end of the knitted bandage.

* * * * *